United States Patent

Manuel Martins Borges De Almeida et al.

(10) Patent No.: US 6,913,358 B2
(45) Date of Patent: Jul. 5, 2005

(54) SYSTEM OF MEASURE THE TOPOGRAPHY OF BOTH CORNEAL SURFACES AND CORNEAL THICKNESS

(75) Inventors: Jose Manuel Martins Borges De Almeida, Braga (PT); Sandra Maria De Braga Franco, Braga (PT)

(73) Assignee: Universidade do Minho, Braga (PT)

(*) Notice: Subject to any disclaimer, the term of this patent is extended or adjusted under 35 U.S.C. 154(b) by 217 days.

(21) Appl. No.: 10/204,638
(22) PCT Filed: Feb. 26, 2001
(86) PCT No.: PCT/PT01/00002

§ 371 (c)(1),
(2), (4) Date: Jan. 3, 2003

(87) PCT Pub. No.: WO01/62140

PCT Pub. Date: Aug. 30, 2001

(65) Prior Publication Data

US 2003/0142270 A1 Jul. 31, 2003

(30) Foreign Application Priority Data

Feb. 25, 2000 (PT) .................................. 102423

(51) Int. Cl.$^7$ .................................................. A61B 3/10
(52) U.S. Cl. ........................................................ 351/212
(58) Field of Search ................................ 351/205, 206, 351/210–212, 214, 221

(56) References Cited

U.S. PATENT DOCUMENTS 6,575,573 B2 * 6/2003 Lai et al. ..................... 351/212

* cited by examiner

Primary Examiner—George Manuel
(74) Attorney, Agent, or Firm—Sughrue Mion, PLLC

(57) ABSTRACT

The invention refers to a system to measure the topography of both surfaces of the cornea (6) and it is thickness, based on a collimated light beam, namely a laser beam, expanded in a fan shape (5) by a cylindrical lens (4) provided with rotational movement. The fan expanded beam (5) produces an image of a corneal section by light diffusion; this image is captured by one or more video cameras (2, 3). The rotation of the cylindrical lens (4) causes the simultaneous rotation of the corneal section image, producing a complete scanning of the same cornea (6).

8 Claims, 1 Drawing Sheet

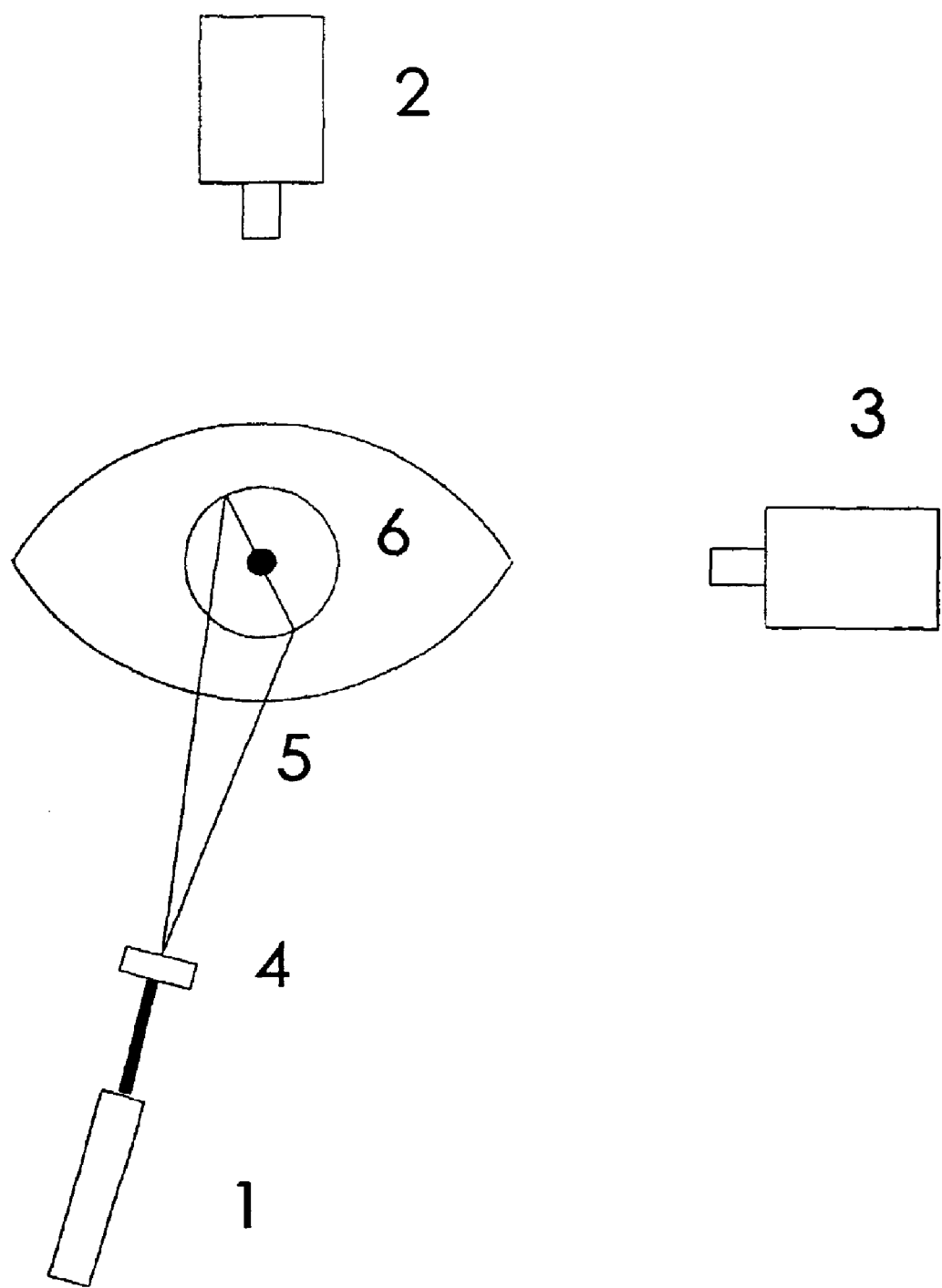

SYSTEM OF MEASURE THE TOPOGRAPHY OF BOTH CORNEAL SURFACES AND CORNEAL THICKNESS

DOMAIN OF THE ART TO WHICH IT REFERS

The invention refers to a system that measures the topography of both corneal surfaces as well as the corneal thickness of the human eyes. Through a collimated light beam, namely a laser beam, expanded in a fan shape, which illuminates the cornea and is provided with movement in order to scan the cornea's entire surface. It also has one or more cameras that collect the images of the diffused light according with an observation angle that is different from the fan expanded beam incidence angle.

STATE OF THE ART

The measurement of corneal topography is of crucial importance for all surgery done in the eyes. In particular, the laser ablation or the keratotomy can only be performed if the exact shape of the cornea is known. The contact lens adaptation, in many cases, also needs previous knowledge of the cornea's topography, namely in corneas with irregular astigmatisms or keratoconus.

There are several commercial equipments that perform corneal topography measurements, in most cases based on a principle known as Placido's disk.

Apart from the external surface topography, the knowledge of the cornea's thickness in each point and consequently, the topography of the internal surface is something that the surgeons, ophthalmologists and optometrists wish and rarely are able to know. The cornea's thickness is usually measured by ultrasonic pachymetry incapable of making a complete map of it's thickness, in every point. There are other pachymeter methods of reduced use and with serious limitations. The complete topography map of both corneal surfaces can be obtained at present with an equipment manufactured by the Orbtek Company, commercially known as Obscan. In this equipment, the cornea is illuminated by the light from a slit lamp and observed by a camera making an angle with the illuminating direction; the slit is subject to a translation movement that permits the scanning of the whole cornea by the illuminating strip that is projected on the surface of the cornea.

Among the known devices, emphasis should be put on the document EP 0630107 that refers to an ophthalmologic instrument for the preceding segment of the eyes.

In a brief description, this invention comprises the following operations: illuminate a portion of the selected cornea, displace the slit through the cornea and generate Tyndall ray trajectories and in this way permit to effectuate the analysis of the optical density of the cornea and the thickness of the cornea. These operations are done through a series of television images of the cornea's optical section produced by a projector that has multiple digitally coded slits. These images are then submitted to a digital analysis.

EXPOSURE OF THE INVENTION

With this method of measurement of the topography of both surfaces of the cornea, a collimated light beam or a laser beam illuminates the cornea, through a small cylindrical lens that provides an expansion of the beam with the shape of a fan and permits an extremely compact and versatile system, when compared to the more conventional slit illuminated systems; besides this it also permits a rotational movement of the light fan, making a rotational scanning of the cornea, which simplifies the mechanical construction and reduces the problems found in processing data acquired by the observation cameras.

ADVANTAGES OF THE INVENTION

This method presents advantages with respect to all methods that measure only the external surface topography, since it delivers also the topography of the internal surface and most of all its thickness. Compared to the slit transversal scanning method, used by Orbscan, it allows the construction of a much more compact, economical to manufacture and predictably more reliable equipment. It also allows the construction of a device which is more mechanically balanced, due to the use of rotational movement instead of the transversal scanning movement. On the other hand, the rotational movement of the light beam allows a much faster scanning than the transversal movement of the previous technique, thus allowing eye movement during the scan to be ignored.

DESCRIPTION OF A METHOD FOR THE REALIZATION OF THE INVENTION

FIG. 1 represents, schematically, a possible implementation of the invention. The laser (1) emits a light beam that is expanded in a fan shape (5) by the small cylindrical lens (4). The fan expanded beam (5) falls upon the cornea (6) and the diffused light is observed by two cameras (2 and 3). The observation planes of the cameras (2 and 3), defined as the planes containing the observation directions and the incidence direction, make an angle of 90° between them.

The cylindrical lens (4) has a rotational movement around the laser axis (1), allowing the fan expanded beam (5) to rotate around itself, defining successive section planes on the cornea (6), all passing through its centre.

The fan expanded beam (5), when falling upon the cornea (6), is diffused by both its surfaces and, with a much lesser intensity, by the cornea thickness itself. This way, both cameras (2 and 3) capture images that are typical of slit lamps, characterised by two luminous arcs and a darker area between them. This image is identical to what is obtained in the normal observation of the eye with the instrument known as slit lamp.

The image in each of the cameras (2 and 3) appears distorted when the plane of corneal section (6) defined by the fan expanded beam (5) is oblique with respect to the observation direction. Only in those cases when the section plane is normal to the observation direction of one of the cameras (2 and 3), that camera has a non-distorted image, while the other camera's image is reduced to a small luminous segment. The conjugation of the images of both cameras (2 and 3) has all the information necessary to reconstruct a non-distorted image to any section plane, as if there was a virtual rotating camera.

Both cameras are connected to an image acquisition and processing equipment, non-illustrated, responsible for removing the distortion from the images. The same equipment processes the non-distorted images to extract profiles from both corneal surfaces, corresponding to successive section planes, and combining them to form the topographic map of both surfaces. Simultaneously, the processing equipment evaluates the thickness map of the cornea.

The previous description is by no means limitative but merely illustrative. The invention should only be considered limited by the spirit and scope of the following claims.

What is claimed is:

1. System for the measurement of the topography of both corneal surfaces and the thickness of the cornea (6), comprising an illumination system comprising a laser (1) or another collimated beam of light and a cylindrical lens (4) to produce an illuminating beam expanded like in the form of a fan (5), the cylindrical lens (4) with rotation in order to rotate the plane of expanded beam (5) and, having at least one observation camera in a different direction than that of the light beam off-axis from the light beam and a system of image acquisition and processing.

2. System for the measurement of the topography of both corneal surfaces and the thickness of the cornea (6), according to claim 1, further comprising two cameras placed in observation planes at a 90° angle, characterized by the combination of the images of the two cameras, allowing the reconstruction of a non-distorted image of the cornea, such as would be obtained by a camera if it were in a plane normal to that of the expanded beam (5).

3. System for the measurement of the topography of both corneal surfaces and the thickness of the cornea (6), according to claim 1, allowing the reconstruction of the topography of both corneal surfaces and the thickness of the cornea, through the processing of a succession of images obtained by rotation of the cylindrical lens (4).

4. System for the measurement of the topography of both corneal surfaces and the thickness of the cornea (6), according to claim 1, further comprising equipment for the acquisition and processing the images of the two cameras, this equipment being responsible for the production of non-distorted images and by the processing of those non-distorted images in order to extract the profiles of both corneal surfaces correspondent to the successive section planes, combining them to form the topographic map of both surfaces.

5. System for the measurement of the topography of both corneal surfaces and the thickness of the cornea (6), comprising having an illumination system comprising a lamp and a rotating slit with optical components to produce an illuminating beam expanded like in the form of a fan (5) for projection onto the cornea, the optical components comprising a cylindrical lens (4) with rotation in order to rotate the plane of expanded beam (5) and, having at least one observation camera off-axis from the light beam and a system of image acquisition and processing.

6. System for the measurement of the topography of both corneal surfaces and the thickness of the cornea (6), according to claim 5, further comprising two cameras placed in observation planes at a 90° angle, characterized by the combination of the images of the two cameras, allowing the reconstruction of a non-distorted image of the cornea, such as would be obtained by a camera if it were in a plane normal to that of the expanded beam (5).

7. System for the measurement of the topography of both corneal surfaces and the thickness of the cornea (6), according to claim 5, allowing the reconstruction of the topography of both corneal surfaces and the thickness of the cornea, through the processing of a succession of images obtained by rotation of the cylindrical lens (4).

8. System for the measurement of the topography of both corneal surfaces and the *thickness of the cornea (6), according to claim 5, further comprising equipment for the acquisition and processing the images of the two cameras, this equipment being responsible for the production of non-distorted images and by the processing of those non-distorted images in order to extract the profiles of both corneal surfaces correspondent to the successive section planes, combining them to form the topographic map of both surfaces.

* * * * *